US012644464B2

(12) United States Patent
Schumacher et al.

(10) Patent No.: US 12,644,464 B2
(45) Date of Patent: Jun. 2, 2026

(54) COMPRESSIBLE ROTOR FOR A FLUID PUMP

(71) Applicant: ECP Entwicklungsgesellschaft mbH, Aachen (DE)

(72) Inventors: Joerg Schumacher, Aachen (DE); Mario Scheckel, Aachen (DE); Henning Schlicht, Aachen (DE)

(73) Assignee: ECP Entwicklungsgesellschaft mbH, Aachen (DE)

( * ) Notice: Subject to any disclaimer, the term of this patent is extended or adjusted under 35 U.S.C. 154(b) by 0 days.

(21) Appl. No.: 19/082,275

(22) Filed: Mar. 18, 2025

(65) Prior Publication Data

US 2025/0305509 A1 Oct. 2, 2025

Related U.S. Application Data

(63) Continuation of application No. 18/239,169, filed on Aug. 29, 2023, now Pat. No. 12,276,285, which is a
(Continued)

(30) Foreign Application Priority Data

Sep. 22, 2009 (EP) ..................................... 09075438

(51) Int. Cl.
*F04D 29/18* (2006.01)
*A61M 60/13* (2021.01)
(Continued)

(52) U.S. Cl.
CPC ........... *F04D 29/181* (2013.01); *A61M 60/13* (2021.01); *A61M 60/205* (2021.01);
(Continued)

(58) Field of Classification Search
CPC ... F04D 2/181; F04D 2/24; F04D 3/00; F05B 2240/311; F05B 2280/6012; A16M 60/13;
(Continued)

(56) References Cited

U.S. PATENT DOCUMENTS

| | | | |
|---|---|---|---|
| 3,464,322 A | | 9/1969 | Pequignot |
| 3,466,220 A | * | 9/1969 | Forbes ...................... B32B 3/12 |
| | | | 428/116 |

(Continued)

FOREIGN PATENT DOCUMENTS

| | | |
|---|---|---|
| CA | 1008330 A | 4/1977 |
| CA | 2311977 A1 | 12/2000 |

(Continued)

OTHER PUBLICATIONS

Hong et al. Processing of Composite Polystyrene Foam with a Honeycomb Structure, 2015, Polymer Engineering and Science (Year: 2015).

(Continued)

*Primary Examiner* — Nathaniel E Wiehe
*Assistant Examiner* — Wayne A Lambert
(74) *Attorney, Agent, or Firm* — Botos Churchill IP Law LLP

(57) ABSTRACT

The invention relates to a rotor for a fluid pump, in particular for use in the medical sphere, the rotor being compressible for bringing to the place of use and thereafter being expandable. The compressibility is assisted by the provision of cavities, in particular also production of the rotor at least partially from a foam.

14 Claims, 5 Drawing Sheets

Related U.S. Application Data continuation of application No. 17/865,064, filed on Jul. 14, 2022, now Pat. No. 11,773,861, which is a continuation of application No. 16/688,187, filed on Nov. 19, 2019, now Pat. No. 11,421,701, which is a continuation of application No. 15/236,757, filed on Aug. 15, 2016, now abandoned, which is a continuation of application No. 13/261,213, filed as application No. PCT/EP2010/005871 on Sep. 22, 2010, now Pat. No. 9,416,783.

(60) Provisional application No. 61/244,614, filed on Sep. 22, 2009.

(51) Int. Cl.

| | |
|---|---|
| *A61M 60/205* | (2021.01) |
| *A61M 60/237* | (2021.01) |
| *A61M 60/414* | (2021.01) |
| *A61M 60/806* | (2021.01) |
| *A61M 60/808* | (2021.01) |
| *A61M 60/825* | (2021.01) |
| *F04D 3/00* | (2006.01) |
| *F04D 29/24* | (2006.01) |
| *A61M 60/135* | (2021.01) |
| *A61M 60/148* | (2021.01) |
| *A61M 60/818* | (2021.01) |

(52) U.S. Cl.
CPC ........ *A61M 60/237* (2021.01); *A61M 60/414* (2021.01); *A61M 60/806* (2021.01); *A61M 60/808* (2021.01); *A61M 60/825* (2021.01); *F04D 3/00* (2013.01); *F04D 29/24* (2013.01); *A61M 60/135* (2021.01); *A61M 60/148* (2021.01); *A61M 60/818* (2021.01); *F05B 2240/311* (2013.01); *F05B 2280/6012* (2013.01)

(58) Field of Classification Search
CPC .............. A16M 60/205; A16M 60/237; A16M 60/414; A16M 60/806; A16M 60/808; A16M 60/825; A16M 60/135; A16M 60/148; A16M 60/818
See application file for complete search history.

(56) References Cited

U.S. PATENT DOCUMENTS

| | | |
|---|---|---|
| 3,510,229 A | 5/1970 | Smith |
| 3,568,659 A | 3/1971 | Karnegis |
| 3,674,019 A | 7/1972 | Grant |
| 3,760,984 A | 9/1973 | Theeuwes |
| 3,802,551 A | 4/1974 | Somers |
| 3,812,812 A | 5/1974 | Hurwitz |
| 3,995,631 A | 12/1976 | Higuchi et al. |
| 4,014,317 A | 3/1977 | Bruno |
| 4,207,028 A | 6/1980 | Ridder |
| 4,299,222 A | 11/1981 | Eckenhoff |
| 4,559,951 A | 12/1985 | Dahl et al. |
| 4,563,181 A | 1/1986 | Wijayarathna et al. |
| 4,679,558 A | 7/1987 | Kensey et al. |
| 4,686,982 A | 8/1987 | Nash |
| 4,727,027 A | 2/1988 | Wiesehahn et al. |
| 4,747,821 A | 5/1988 | Kensey et al. |
| 4,749,376 A | 6/1988 | Kensey et al. |
| 4,753,221 A | 6/1988 | Kensey et al. |
| 4,788,925 A | 12/1988 | Simon et al. |
| 4,797,312 A | 1/1989 | Sherwood |
| 4,801,243 A | 1/1989 | Norton |
| 4,817,613 A | 4/1989 | Jaraczewski et al. |
| 4,846,152 A | 7/1989 | Wampler et al. |
| 4,919,647 A | 4/1990 | Nash |
| 4,957,504 A | 9/1990 | Chardack |
| 4,969,865 A | 11/1990 | Hwang et al. |
| 4,995,857 A | 2/1991 | Arnold |
| 5,002,531 A | 3/1991 | Bonzel |
| 5,011,469 A | 4/1991 | Buckberg et al. |
| 5,040,944 A | 8/1991 | Cook |
| 5,042,984 A | 8/1991 | Kensey et al. |
| 5,052,404 A | 10/1991 | Hodgson |
| 5,061,256 A | 10/1991 | Wampler |
| 5,092,844 A | 3/1992 | Schwartz et al. |
| 5,097,849 A | 3/1992 | Kensey et al. |
| 5,108,411 A | 4/1992 | Mckenzie |
| 5,112,292 A | 5/1992 | Hwang et al. |
| 5,113,872 A | 5/1992 | Jahrmarkt et al. |
| 5,117,838 A | 6/1992 | Palmer et al. |
| 5,118,264 A | 6/1992 | Smith |
| 5,145,333 A | 9/1992 | Smith |
| 5,154,724 A | 10/1992 | Andrews |
| 5,163,910 A | 11/1992 | Schwartz et al. |
| 5,169,378 A | 12/1992 | Figuera |
| 5,183,384 A | 2/1993 | Trumbly |
| 5,191,888 A | 3/1993 | Palmer et al. |
| 5,201,679 A | 4/1993 | Velte et al. |
| 5,275,580 A | 1/1994 | Yamazaki |
| 5,308,325 A | 5/1994 | Quinn et al. |
| 5,308,356 A | 5/1994 | Blackshear et al. |
| 5,330,528 A | 7/1994 | Lazim |
| 5,373,619 A | 12/1994 | Fleischhacker et al. |
| 5,376,114 A | 12/1994 | Jarvik |
| 5,383,840 A | 1/1995 | Heilman et al. |
| 5,439,444 A | 8/1995 | Andersen et al. |
| 5,458,575 A | 10/1995 | Wang |
| 5,470,320 A | 11/1995 | Tiefenbrun et al. |
| 5,501,574 A | 3/1996 | Raible |
| 5,531,789 A | 7/1996 | Yamazaki et al. |
| 5,599,306 A | 2/1997 | Klein et al. |
| 5,701,911 A | 12/1997 | Sasamine et al. |
| 5,749,855 A | 5/1998 | Reitan |
| 5,755,784 A | 5/1998 | Jarvik |
| 5,776,190 A | 7/1998 | Jarvik |
| 5,797,948 A | 8/1998 | Dunham |
| 5,813,405 A | 9/1998 | Montano et al. |
| 5,820,571 A | 10/1998 | Erades et al. |
| 5,851,174 A | 12/1998 | Jarvik et al. |
| 5,863,284 A * | 1/1999 | Klein ................... A61N 5/1002 600/3 |
| 5,882,329 A | 3/1999 | Patterson et al. |
| 5,888,241 A | 3/1999 | Jarvik |
| 5,938,672 A | 8/1999 | Nash |
| 6,030,397 A | 2/2000 | Monetti et al. |
| 6,129,704 A | 10/2000 | Forman et al. |
| 6,152,693 A | 11/2000 | Olsen et al. |
| 6,168,624 B1 | 1/2001 | Sudai |
| 6,245,007 B1 | 6/2001 | Bedingham et al. |
| 6,254,359 B1 | 7/2001 | Aber |
| 6,302,910 B1 | 10/2001 | Yamazaki et al. |
| 6,308,632 B1 | 10/2001 | Shaffer |
| 6,336,939 B1 | 1/2002 | Yamazaki et al. |
| 6,346,120 B1 | 2/2002 | Yamazaki et al. |
| 6,387,125 B1 | 5/2002 | Yamazaki et al. |
| 6,482,228 B1 | 11/2002 | Norred |
| 6,503,224 B1 | 1/2003 | Forman et al. |
| 6,506,025 B1 | 1/2003 | Gharib |
| 6,508,787 B2 | 1/2003 | Erbel et al. |
| 6,517,315 B2 | 2/2003 | Belady |
| 6,527,521 B2 | 3/2003 | Noda |
| 6,533,716 B1 | 3/2003 | Schmitz-rode et al. |
| 6,537,030 B1 | 3/2003 | Garrison |
| 6,537,315 B2 | 3/2003 | Yamazaki et al. |
| 6,544,216 B1 | 4/2003 | Sammler et al. |
| 6,547,787 B1 | 4/2003 | Altman et al. |
| 6,592,612 B1 | 7/2003 | Samson et al. |
| 6,616,596 B1 | 9/2003 | Milbocker |
| 6,652,548 B2 | 11/2003 | Evans et al. |
| 6,719,791 B1 | 4/2004 | Nuesser et al. |
| 6,860,713 B2 | 3/2005 | Hoover |
| 6,945,977 B2 | 9/2005 | Demarais et al. |
| 6,976,996 B1 | 12/2005 | Aboul-hosn |
| 6,981,942 B2 | 1/2006 | Khaw et al. |

(56) References Cited

U.S. PATENT DOCUMENTS

| | | | |
|---|---|---|---|
| 7,022,100 B1 | 4/2006 | Aboul-hosn et al. |
| 7,027,875 B2 | 4/2006 | Siess et al. |
| 7,074,018 B2 | 7/2006 | Chang |
| 7,179,273 B1 | 2/2007 | Palmer et al. |
| 7,335,193 B2 | 2/2008 | Wong et al. |
| 7,393,181 B2 | 7/2008 | Mcbride et al. |
| 7,425,288 B2 | 9/2008 | Flodin et al. |
| 7,467,929 B2 | 12/2008 | Nuesser et al. |
| 7,481,803 B2 | 1/2009 | Kesten et al. |
| 7,611,887 B2 | 11/2009 | Cinquin et al. |
| 7,731,675 B2 | 6/2010 | Aboul-hosn et al. |
| 7,878,967 B1 | 2/2011 | Khanal |
| 7,927,068 B2 | 4/2011 | Mcbride et al. |
| 7,934,909 B2 | 5/2011 | Nuesser et al. |
| 8,079,948 B2 | 12/2011 | Shifflette |
| 8,449,443 B2 | 5/2013 | Rodefeld et al. |
| 8,550,088 B1 | 10/2013 | Booher |
| 8,849,398 B2 | 9/2014 | Evans |
| 8,926,492 B2 | 1/2015 | Scheckel |
| 9,162,017 B2 | 10/2015 | Evans et al. |
| 10,729,833 B2 | 8/2020 | Higgins |
| 2002/0123661 A1 | 9/2002 | Verkerke et al. |
| 2003/0135086 A1 | 7/2003 | Khaw et al. |
| 2003/0231959 A1 | 12/2003 | Snider |
| 2004/0034320 A1 | 2/2004 | Burnett |
| 2004/0044266 A1 | 3/2004 | Siess et al. |
| 2004/0046466 A1 | 3/2004 | Siess et al. |
| 2004/0093074 A1 | 5/2004 | Hildebrand et al. |
| 2004/0127813 A1 | 7/2004 | Schwamm |
| 2004/0215222 A1 | 10/2004 | Krivoruchko |
| 2004/0215228 A1 | 10/2004 | Simpson et al. |
| 2005/0202207 A1 | 9/2005 | Inaba |
| 2006/0008349 A1 | 1/2006 | Khaw |
| 2006/0030809 A1 | 2/2006 | Barzilay et al. |
| 2006/0155305 A1 | 7/2006 | Freudenthal et al. |
| 2006/0195004 A1 | 8/2006 | Jarvik |
| 2008/0114339 A1 | 5/2008 | Mcbride et al. |
| 2008/0132747 A1 | 6/2008 | Shifflette |
| 2008/0132748 A1 | 6/2008 | Shifflette |
| 2008/0262584 A1 | 10/2008 | Bottomley et al. |
| 2008/0306327 A1 | 12/2008 | Shifflette |
| 2009/0012603 A1 | 1/2009 | Xu et al. |
| 2009/0093764 A1 | 4/2009 | Pfeffer et al. |
| 2009/0093796 A1 | 4/2009 | Pfeffer et al. |
| 2009/0112050 A1 | 4/2009 | Farnan et al. |
| 2009/0112312 A1 | 4/2009 | Larose et al. |
| 2010/0041939 A1 | 2/2010 | Siess |
| 2010/0241229 A1 | 9/2010 | Ruffieux et al. |
| 2010/0268017 A1 | 10/2010 | Siess |
| 2011/0236210 A1 | 9/2011 | Mcbride et al. |
| 2011/0238172 A1 | 9/2011 | Akdis |
| 2011/0240194 A1 * | 10/2011 | Summers .................. B60C 9/18 |
| | | 428/116 |
| 2011/0275884 A1 | 11/2011 | Scheckel |
| 2012/0039711 A1 | 2/2012 | Roehn |
| 2012/0039713 A1 | 2/2012 | Shifflette |
| 2012/0041254 A1 | 2/2012 | Scheckel |
| 2012/0046648 A1 | 2/2012 | Scheckel |
| 2012/0093628 A1 | 4/2012 | Liebing |
| 2012/0101455 A1 | 4/2012 | Liebing |
| 2012/0142994 A1 | 6/2012 | Toellner |
| 2012/0184803 A1 | 7/2012 | Simon et al. |
| 2012/0224970 A1 | 9/2012 | Schumacher et al. |
| 2012/0234411 A1 | 9/2012 | Scheckel |
| 2012/0237353 A1 | 9/2012 | Schumacher et al. |
| 2012/0237357 A1 | 9/2012 | Schumacher et al. |
| 2012/0264523 A1 | 10/2012 | Liebing |
| 2012/0265002 A1 | 10/2012 | Roehn et al. |
| 2012/0294727 A1 | 11/2012 | Roehn |
| 2012/0301318 A1 | 11/2012 | Er |
| 2012/0308406 A1 | 12/2012 | Schumacher |
| 2013/0019968 A1 | 1/2013 | Liebing |
| 2013/0041202 A1 | 2/2013 | Toellner |
| 2013/0060077 A1 | 3/2013 | Liebing |
| 2013/0066139 A1 | 3/2013 | Wiessler et al. |
| 2013/0085318 A1 | 4/2013 | Toellner |
| 2013/0177409 A1 | 7/2013 | Schumacher et al. |
| 2013/0177432 A1 | 7/2013 | Toellner et al. |
| 2013/0204362 A1 | 8/2013 | Toellner et al. |
| 2013/0237744 A1 | 9/2013 | Pfeffer et al. |
| 2014/0039465 A1 | 2/2014 | Schulz et al. |
| 2014/0255176 A1 | 9/2014 | Bredenbreuker et al. |
| 2020/0405926 A1 | 12/2020 | Alexander et al. |

FOREIGN PATENT DOCUMENTS

| | | | | |
|---|---|---|---|---|
| CN | 1197503 C | 4/2005 | | |
| CN | 201209588 Y | 3/2009 | | |
| DE | 2113986 A1 | 9/1972 | | |
| DE | 2340755 A | 2/1975 | | |
| DE | 4124299 A1 | 1/1992 | | |
| DE | 19535781 A1 | 3/1997 | | |
| DE | 19711935 A1 | 4/1998 | | |
| DE | 10059714 C1 | 5/2002 | | |
| DE | 10108810 A1 | 8/2002 | | |
| DE | 10155011 A1 | 5/2003 | | |
| DE | 10336902 B3 | 8/2004 | | |
| DE | 102010011998 A1 | 9/2010 | | |
| DE | 102014201375 A1 * | 7/2015 | ............ | B62D 29/04 |
| EP | 0480102 A1 | 4/1992 | | |
| EP | 0560000 A2 | 9/1993 | | |
| EP | 0629412 A2 | 12/1994 | | |
| EP | 0768091 A1 | 4/1997 | | |
| EP | 0884064 A2 | 12/1998 | | |
| EP | 0914171 A2 | 5/1999 | | |
| EP | 0916359 A1 | 5/1999 | | |
| EP | 951302 A2 | 10/1999 | | |
| EP | 1114648 A2 | 7/2001 | | |
| EP | 2218469 A1 | 8/2010 | | |
| EP | 2229965 A1 | 9/2010 | | |
| EP | 2301598 A1 | 3/2011 | | |
| EP | 2308524 A1 | 4/2011 | | |
| EP | 2343091 A1 | 7/2011 | | |
| EP | 2345440 A1 | 7/2011 | | |
| EP | 2366412 A2 | 9/2011 | | |
| EP | 2497521 A1 | 9/2012 | | |
| EP | 2606919 A1 | 6/2013 | | |
| EP | 2606920 A1 | 6/2013 | | |
| EP | 2607712 A1 | 6/2013 | | |
| GB | 2239675 A | 7/1991 | | |
| RU | 2229899 C2 | 6/2004 | | |
| WO | 9202263 A1 | 2/1992 | | |
| WO | 9302732 A1 | 2/1993 | | |
| WO | 9303786 A1 | 3/1993 | | |
| WO | 9314805 A1 | 8/1993 | | |
| WO | 94001148 A1 | 1/1994 | | |
| WO | 9405347 A1 | 3/1994 | | |
| WO | 9409835 A1 | 5/1994 | | |
| WO | 9420165 A2 | 9/1994 | | |
| WO | 9523000 A2 | 8/1995 | | |
| WO | 9618358 A1 | 6/1996 | | |
| WO | 9625969 A2 | 8/1996 | | |
| WO | 9744071 A1 | 11/1997 | | |
| WO | 9853864 A1 | 12/1998 | | |
| WO | 9917819 A1 | 4/1999 | | |
| WO | 9919017 A1 | 4/1999 | | |
| WO | 0027446 A1 | 5/2000 | | |
| WO | 0043054 A2 | 7/2000 | | |
| WO | 0062842 A1 | 10/2000 | | |
| WO | 2001007760 A1 | 2/2001 | | |
| WO | 2001007787 A1 | 2/2001 | | |
| WO | 2001083016 A2 | 11/2001 | | |
| WO | 2003057013 A2 | 7/2003 | | |
| WO | 2003103745 A2 | 12/2003 | | |
| WO | 2005002646 A1 | 1/2005 | | |
| WO | 2005016416 A1 | 2/2005 | | |
| WO | 2005021078 A1 | 3/2005 | | |
| WO | 2005030316 A1 | 4/2005 | | |
| WO | 2005032620 A1 | 4/2005 | | |
| WO | 2005081681 A2 | 9/2005 | | |
| WO | 2006020942 A1 | 2/2006 | | |
| WO | 2006034158 A2 | 3/2006 | | |
| WO | 2006133209 A1 | 12/2006 | | |
| WO | 2007003351 A1 | 1/2007 | | |

(56)     References Cited

FOREIGN PATENT DOCUMENTS

| WO | 2007103390 | A2 | 9/2007 |
|----|-----------|----|--------|
| WO | 2007103464 | A2 | 9/2007 |
| WO | 2007112033 | A2 | 10/2007 |
| WO | 2008017289 | A2 | 2/2008 |
| WO | 2008034068 | A2 | 3/2008 |
| WO | 2008054699 | A2 | 5/2008 |
| WO | 2008106103 | A2 | 9/2008 |
| WO | 2008116765 | A2 | 10/2008 |
| WO | 2008124696 | A1 | 10/2008 |
| WO | 2008137352 | A1 | 11/2008 |
| WO | 2008137353 | A1 | 11/2008 |
| WO | 2009003294 | A1 | 1/2009 |
| WO | 2009015784 | A1 | 2/2009 |
| WO | 2009029959 | A2 | 3/2009 |
| WO | 2010133567 | A1 | 11/2010 |
| WO | 2013034547 | A1 | 3/2013 |
| WO | 2013092971 | A1 | 6/2013 |
| WO | 2013093058 | A1 | 6/2013 |

OTHER PUBLICATIONS

International Search Report and Written Opinion for International Application No. PCT/EP2010/005871 dated Mar. 22, 2011 (6 pp.).

Sivertsen Polymer Foams, 2007, Springer (Year: 2007).

Office Action issued in European Application No. 23 159 838.4 dated Apr. 4, 2025 (17 pp.).

* cited by examiner

COMPRESSIBLE ROTOR FOR A FLUID PUMP

CROSS-REFERENCE TO RELATED APPLICATIONS

This application is a continuation of U.S. patent application Ser. No. 18/239,169, filed Aug. 29, 2023, now U.S. Pat. No. 12,276,285, which is a continuation of U.S. patent application Ser. No. 17/865,064, filed Jul. 14, 2022, now U.S. Pat. No. 11,773,861, which is a continuation of U.S. patent application Ser. No. 16/688,187, filed Nov. 19, 2019, now U.S. Pat. No. 11,421,701, which is a continuation of U.S. patent application Ser. No. 15/236,757, filed Aug. 15, 2016, now abandoned, which is a continuation of U.S. patent application Ser. No. 13/261,213, filed May 16, 2012, now U.S. Pat. No. 9,416,783, which is a National Stage filing under 35 U.S.C. § 371 of International Application No. PCT/EP2010/005871, filed Sep. 22, 2010, published in English, which claims the benefit of U.S. Provisional Patent Application No. 61/244,614, filed Sep. 22, 2009, and European Patent Application No. 09075438.3, filed Sep. 22, 2009. The disclosures of each of the foregoing applications are incorporated herein by reference in their entirety.

BACKGROUND OF THE INVENTION

The present invention resides in the field of mechanical engineering, in particular precision engineering, and relates to rotors for fluid pumps.

Rotary pumps are common knowledge but these are constantly being improved, in particular for special applications. Thus axial pumps have become known which have a rotor conveying fluid in the axial direction in a housing, rotor and housing being deformable, advantageously compressible, in order to bring these before operation to a desired place of use which is difficult to access and in order to decompress and operate them there.

Such pumps are used for example in medicine in micro-construction form in order to be introduced into the body of a patient, for example via the bloodstream, and to be operated there either in a blood vessel or in a ventricle.

The pumps can be compressed such that they can be pushed through the blood vessel and then possibly decompressed in a larger body cavity in order to bring the rotor to unfold and to achieve a high conveying power.

A compressible rotor is known for example from U.S. Pat. No. 6,860,713.

Another rotor is known from U.S. Pat. No. 7,393,181 B2. The known solutions are based either on the elasticity and deformability of the material of the rotor or on mechanical constructions, such as the provision of bent places or joints for folding and unfolding the individual components.

Such constructions often have the disadvantage that the compressibility is limited since for example the hub of a rotor remains unchanged, that complex joints must be provided which are stabilised during operation and that partially super-elastic materials are used, such as memory alloys which change their shape as a function of the ambient temperature.

These constructions often make the use of composite materials necessary, and it is difficult, during construction of support constructions, not to impede the flow of the fluid to be conveyed and possibly to preclude as far as possible also damage to the fluid. This is important in particular when conveying blood which contains highly functional and also mechanically susceptible components.

BRIEF SUMMARY OF THE INVENTION

The object underlying the invention against the background of the state of the art is to produce a rotor in the simplest possible manner, which has a constructionally simple structure, is compressible reversibly to a high degree and is reliable in operation.

The object is achieved according to the invention by the features of patent claim 1.

The rotor according to the invention for a fluid pump has at least one blade and at least one deformable cavity which is filled or can be filled with a fluid.

As a result, a volume compressibility of the rotor is produced, which leads per se, during compression, already to a reduction in the rotor volume and possibly the rotor diameter. In addition, the various components of the rotor, such as for example blades, can still be bent and pressed in the direction of the rotor axis in order to reduce the diameter further.

The rotor is hence distinguished by a material mixture or a material which can be converted by compression from a first, lower density or from a first, lower specific weight to a second, higher density or a higher specific weight. The cavities can thereby be closed and filled with a gas, such as for example air or nitrogen, or a noble gas or another bioinert gas which can be compressed easily in volume by pressure.

Such closed cavities tend to expand again in the absence of an external pressure force due to the gas elasticity so that the rotor, as soon as it is brought to the place of use, can unfold again automatically. At least the unfolding movement is assisted however by the gas elasticity.

In addition, gas lines to the rotor can however be provided, which gas lines end in one or more cavities and actively allow the cavities to be pumped up. The gas for the compression can possibly also be suctioned out via the same lines.

Likewise, the operation can take place with a liquid if this is introduced into the cavities. If a liquid is situated in the cavities, then this is normally very much less compressible but, due to suitable choice of the viscosity in cooperation with the remaining constructional parts of the rotor, it can enable high moveability and hence compressibility and nevertheless support a certain rotor stability during operation due to the incompressibility after unfolding of the rotor.

The cavities can also have an open design, hence high compressibility likewise being provided. The material which delimits the cavities must then have a corresponding elastic configuration. This can be provided for example with an open-pore foam.

The invention can also be implemented advantageously by the cavity/cavities being at least partially delimited by a partially permeable membrane.

For this purpose, a body consisting of an. open-pore foam can be sealed at the outside thereof at least partially by a semipermeable membrane or a closed-pore foam can consist of a partially permeable material. Through the membranes, a material transport can be respectively effected specifically, which material transport fills or empties the cavity/cavities and hence effects or assists expansion/compression of the body.

A cavity can be filled with a liquid which, together with the membrane used and as a function of the liquid in which the pump can be inserted, in particular human blood, allows diffusion into the cavity/cavities as a result of osmosis, which leads to an increase in pressure and to pumping-up of the rotor.

Likewise, also materials can be used as cavity-delimiting material or as a filler of the cavities, which, after coming in contact with the liquid to be conveyed, lead to swelling processes as a result of absorption of the liquid and hence assist decompression of the rotor via an increase in volume.

As partially permeable membrane for delimiting cavities, there can be used, according to the used filling materials for the cavities and the materials which are intended to be allowed through or held back, membranes of microfiltration (0.5-0.1 µm particle size), ultrafiltration (0.1-0.01 µm particle size) and nanofiltration (1-10 nm). Independently of the particle size, basically biological or synthetic membrane materials can be used (as biological materials, for example Cuprophan, Hemophan or cellulose triacetate, as synthetic membrane, for example Teflon or Goretex.

Synthetic materials in general have a higher water permeability and are themselves often hydrophobic. There can be used as synthetic materials, polysylphone, polyamide, polyacrylonitrile and also copolymers thereof and also polymethylmethacrylates, polytetrafluoroethylene and derivatives thereof.

High-flux membranes are advantageously used, which allow through molecules up to a molecular weight of 50,000 Dalton and which ensure rapid material transport.

Advantageously, the material is chosen such that it retains germs/bacteria/microorganisms preventing contamination or infection.

In the case of an osmosis process, filling the cavities with a salt or a salt solution, the salt concentration of which is higher than that of the liquids to be conveyed, is possible.

Advantageously, it can also be provided that at least the predominant part of the cavities is/are surrounded by solid material of the rotor and connected to each other via openings. In this case, during compression, a fluid transport can take place via the cavities and possibly also out of the rotor so that the corresponding cavities can be easily compressed entirely.

The rotor can consist for example partially of a porous material, such as foam, in particular polyurethane. Such a foam can be open-or closed-pore. In the case of an open-pore foam, the elasticity is based on the supporting material which surrounds the pores and moves after compression by itself back into its original form, the gas or fluid being able to flow back into the pores, and/or based on the elasticity of a filler gas if the open-pore foam body is surrounded entirely by an impermeable or partially permeable outer layer. Due to the limited flow cross-sections of the connections of the cavities/pores to each other, a time constant in the compression/decompression can be chosen within specific limits. This can ensure, during operation of the pump, that sudden deformations of the rotor due to irregular mechanical loading are counteracted.

The invention can advantageously also provide that the rotor has at least one cavity which has a greater extension in a first direction than in the directions essentially perpendicular thereto.

Provision of such anisotropic cavities, with correct positioning, also permits production of anisotropic mechanical properties of the rotor. As a result, it is possible to design the latter to be compressible radially in a simple manner and with low force expenditure without the same slight deformability occurring during operation due to the dynamic resistance of the fluid to be conveyed.

During operation, the rotor is hence stabilised relative to the forces acting axially and in the circumferential direction whilst it offers relatively low resistances to radial compression.

The corresponding cavities can be configured, in cross-section, to be for example round, hexagonal, triangular or square and have for example a strand shape so that their cross-section is essentially the same overall along its length. As a result, symmetry which serves for stability of the rotor is produced.

Corresponding cavities can be provided for example particularly advantageously in at least one blade since said cavities carry the largest proportion of the diameter reduction of the rotor, on the one hand, and, on the other hand, are subjected to the highest dynamic forces during operation.

However, the blade can have such a stable configuration that it is self-supporting and a hub can even be dispensed with. Such a blade can be configured for example as a flat body, which is bent in a spiral about an axis, in particular made of foam. For example, for production thereof, a polyurethane foam plate can be cut, as desired, in a flat shape, thereafter rotated about an axis and then hardened or stiffened. The shape of the blade is hence stabilised but an elastic compressibility is provided furthermore.

However it can also be provided to produce such a blade or an entire rotor by spraying a foam into a pre-manufactured mould.

The invention can also be used with rotors provided with hubs and, in this case, the hub body in particular can have the cavities according to the invention or be produced at least partially from a foam.

If anisotropic cavities are provided in the rotor, then it is advantageous to align these in the direction of their greatest stability along the force/stress extension lines which arise within the rotor during operation.

For example, the longitudinal axes of strand-shaped cavities, such as for example honeycomb bodies, can be orientated perpendicular to the blade surface in order to support forces acting in this direction or circumferential direction.

The object of producing a rotor which has as simple a construction as possible, which is compressible to a high degree (in particular reversibly) and is reliable in operation is achieved in addition by a compressible rotor for a fluid pump having at least one blade, the rotor being constructed such that it can adopt a compressed and a decompressed state and the average change in density of the rotor material between compressed and decompressed state is at least 10%.

It is hereby important, as a delimitation from the state of the art, that the volume change occurs above all also by changes in the density of the rotor material. What is involved here therefore is not merely elastic deformation processes in which the average density of the rotor material is essentially constant. The mentioned change in density is "temperature-adjusted", i.e. it is the change in density with a warm rotor at e.g. 36° C. which is the basis for the compressed and decompressed state.

In order to produce this change in density, the approaches mentioned in this application can be chosen. Both reversible and irreversible methods are hereby considered. These are e.g. osmotic processes, however also processes in which open-pore or closed-pore foam is used.

The change in density of the rotor need not be uniform at all places, for example it is possible that, in the region of a hub or of the blade, a smaller change in density is achieved because of the possibly desired higher rigidity there and, in the region of a virtual "joint" between hub and blade, a stronger compression takes place.

The average change in density of the entire rotor can preferably also be even greater, for example at least 15%, alternatively at least 20%. With respect to a plastic material, starting values, by way of example, for the density are 0.01 . . . 2 g/cm$^3$ in the decompressed state and 0.05 . . . 3 g/cm$^3$ in the compressed state.

The invention relates, apart from to a rotor of the described type, also to a fluid pump having such a rotor, in which a compressible housing surrounding the rotor is provided.

According to the invention, the housing can consist at least partially also of a material which has cavities, in particular a foam, for example polyurethane. In this way, the housing can be compressed and decompressed simply together with the rotor.

BRIEF DESCRIPTION OF THE DRAWINGS

The invention is shown in a drawing and subsequently described with reference to an embodiment in the following. There are thereby shown FIG. 1 a schematic view of an axial pump in use in the body of a patient, FIG. 2 an enlarged view of a pump, partially in longitudinal section, FIG. 3 a rotor in three-dimensional view with hub, FIG. 4 a rotor without hub in three-dimensional view, FIG. 5 a part of a blade in a partially opened-up representation with honeycomb-shaped cavities, FIG. 6 a section through a porous material, FIG. 7 three-dimensionally, a possible shape of cavities, FIG. 8 three-dimensionally, a further possible shape of cavities, FIG. 9 a structure having circular cylindrical cavities, FIG. 10 a structure having hexagonal honeycomb-shaped cavities in the densest arrangement and FIG. 11 a structure having octagonal honeycomb-shaped spaces and further cavities situated therebetween.

DETAILED DESCRIPTION

Figure 1:
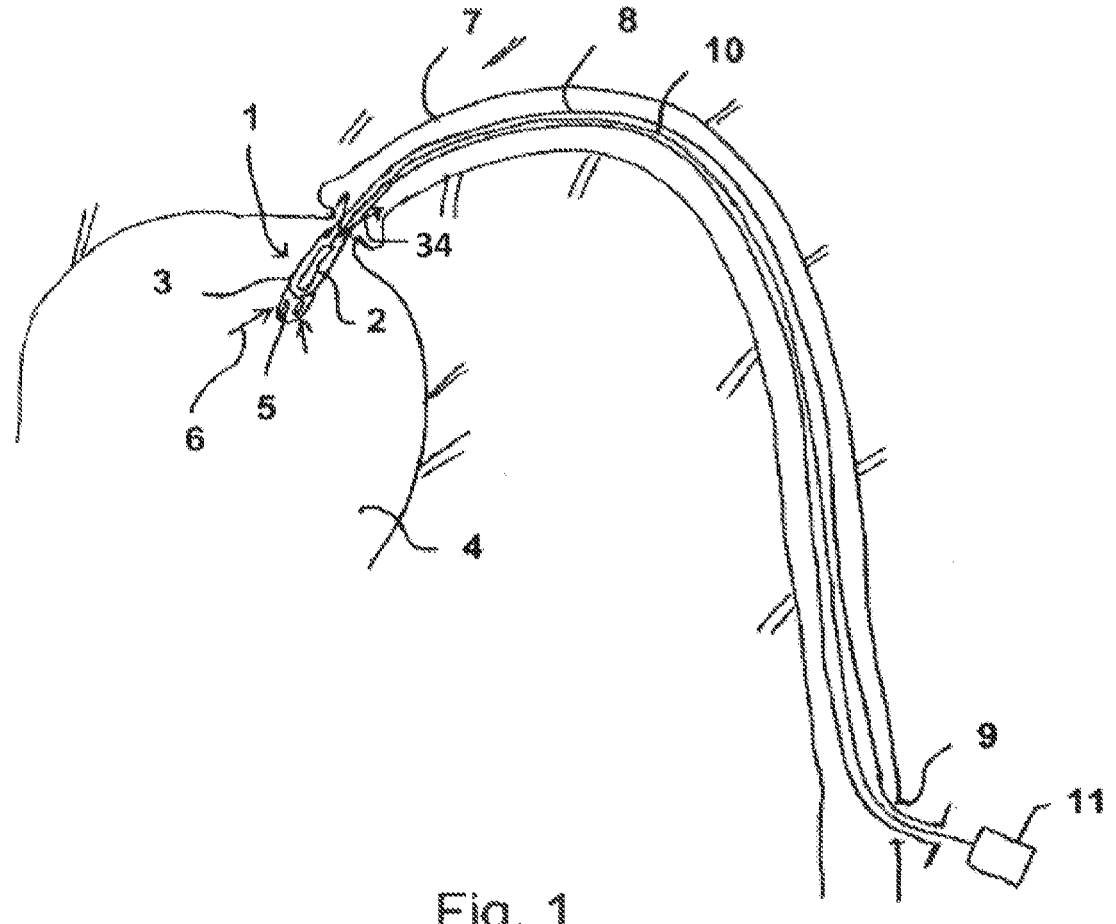

FIG. 1 shows an axial pump having a rotor 2 and a housing 3 in the interior of a ventricle 4 in schematic view.

Within the ventricle 4, blood is suctioned in through openings 5 by the pump 1 as indicated by the arrows 6. The blood is expelled again in the direction of the arrows 34 within a blood vessel 7 and hence the pumping function of the heart is replaced or assisted.

The pump 1 is disposed at the distal end of a hollow catheter 8 which is inserted through the blood vessel 7 into the ventricle 4 and the proximal end thereof protrudes through a lock 9 out of the blood vessel and ultimately out of the body of the patient.

A drive shaft 10 which can be actuated, with a high speed of rotation, typically above 10,000 revolutions per minute, by means of a motor 11 which is disposed outside the body, is provided within the hollow catheter 8. In the pump 1, the rotor 2 is connected to the shaft 10 and rotates with the latter.

The pump 1 has a greater diameter during operation within the ventricle 4 than during introduction through the blood vessel 7. It can have in particular a greater diameter than the inner diameter of the blood vessel.

In order to remove the pump from the body, the latter is compressed again and retracted through the lock 9.

Figure 2:
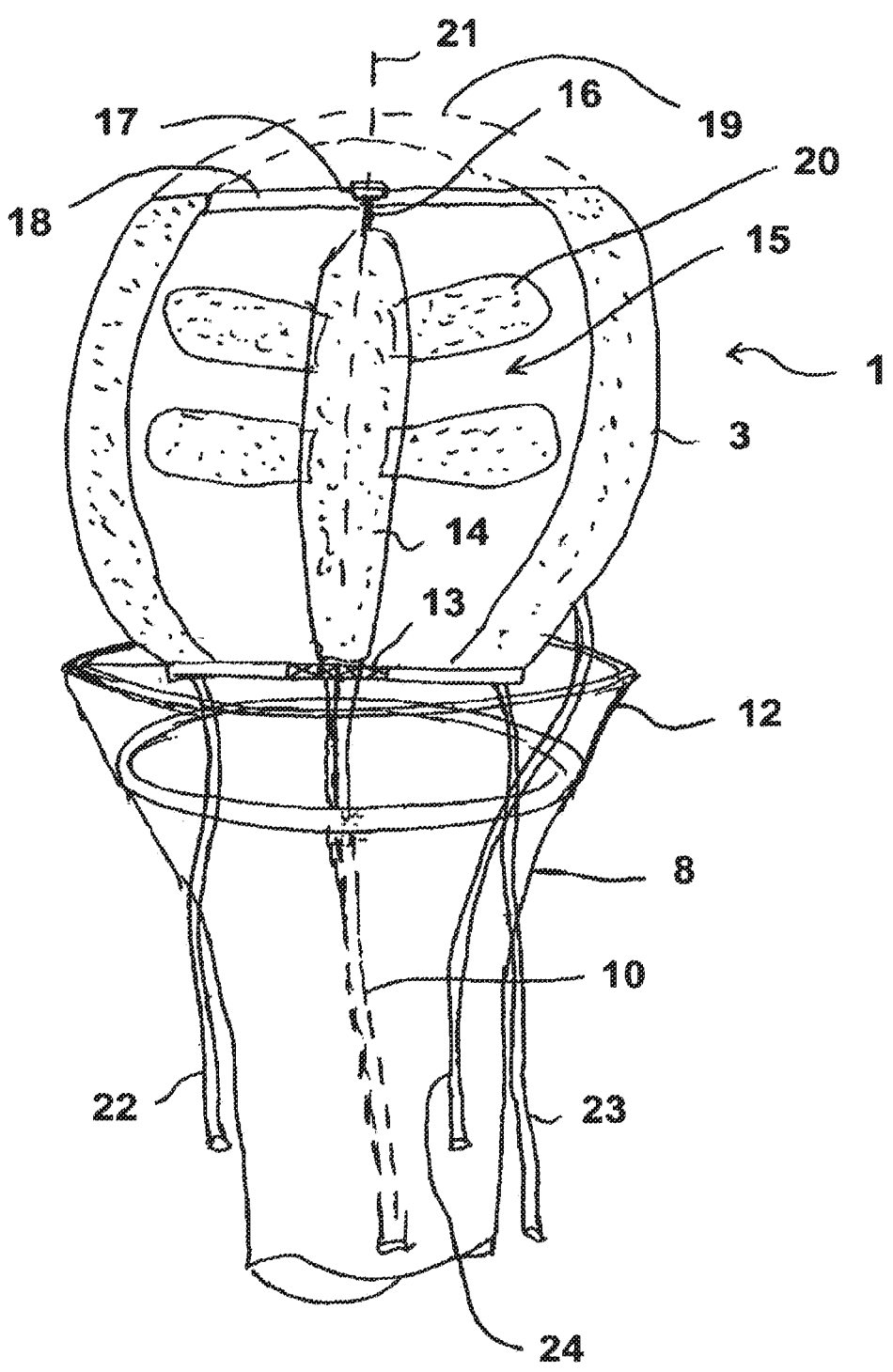

FIG. 2 shows schematically the pump in enlarged form, the end of the hollow catheter 8 being illustrated in the lower region with a compression funnel 12.

The shaft 10 extends through the hollow catheter 8 and is mounted rotatably in a bearing 13 at the proximal end of the pump housing 3. The bearing can be designed such that it has a tension-resistant configuration so that the pump housing 3 can be retracted on the shaft 10 at least some distance into the compression funnel 12 and hence is radially compressible at the same time. The housing can also be retractable by means of an additional cable extending through the hollow catheter.

The shaft 10 is connected to the hub body 14 of the rotor 15 which, for its part, is mounted either directly or via a shaft extension 16 on the distal end of the pump housing 3, once again rotatably in a second bearing 17. This bearing also can have a tension-resistant configuration in order to transmit tensile forces by means of the shaft 10 and the rotor 15 to the housing.

The mounting 17 is secured in a strut arrangement 18 of the pump housing 3, which strut arrangement has sufficient openings to allow blood or other body fluids to flow in towards the rotor.

The front contour of the pump housing is designated with 19 and has a grating-shaped configuration in order, on the one hand, to avoid direct contact with the rotor when the pump strikes against the body tissue and, on the other hand, to keep larger particles remote during suction.

When introducing the pump, firstly the pump housing 3 and the rotor 15 can be greatly compressed radially and mounted at the distal end of the hollow catheter 8 in the latter. After introduction into a ventricle, the pump can be pushed some distance out of the catheter 8 by means of the shaft and unfold automatically because of elastic effect. The pump housing 3 thereby unfolds to the illustrated diameter and, at the same time, the blades 20 are raised away from the hub body 14 and are removed from the axis of rotation 21.

The pushing of the pump 1 out of the hollow catheter 8 can be achieved, alternatively or additionally to the thrust movement via the shaft 10, also by means of further cables 22, 23 which are guided closely in or on the hollow catheter and hence allow both tensile and pressure movements. These cables 22, 23 can be secured at the proximal end outside the patient's body on a manipulation ring which can be pushed and pulled from outside. The cables can be guided close to and axially displaceably in guides on the outside of the hollow catheter.

The pump housing 3 can consist of an open-pore foam or a closed-pore foam and consequently have an elastic configuration. However, also larger cavities can be provided there, which have a fluid suctioned out or are filled with a fluid for example by means of a hose 24 which is connected at the proximal end to a gas reservoir or a pump in order to compress or expand/decompress the pump.

By means of the compression movement of the housing, also the rotor 15 can be compressed by pressure exerted radially thereon. However, the rotor can also be compressed automatically likewise by suction of a fluid out of corresponding cavities or its compression can at least be assisted by such. an effect.

A corresponding compression and decompression effect can however be provided also solely by pushing the pump out of the hollow catheter and inserting it into the compression connection pipe 12.

Figures 3, 4:
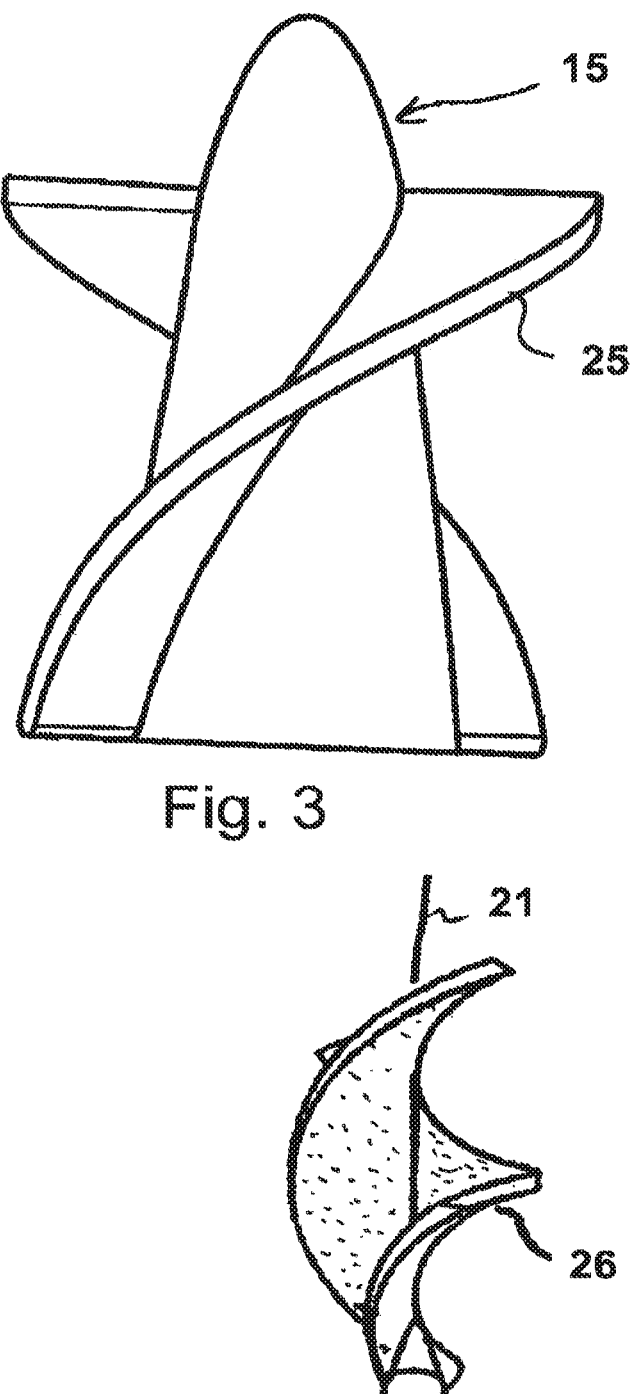

In FIG. 3, a rotor having a circumferential blade 25 is shown in three-dimensional view, rotor and blade being able to be produced in one piece, for example from a foam material, e.g. made of polyurethane. Alternatively or additionally thereto, also larger cavities can be provided, in particular in the hub, but also in the blade 25.

FIG. 4 shows a blade 26 which is self-supporting, for example it can consist of a foam and have a hub-free design. It is cut for example out of a flat material and rotates at the proximal and distal end mutually about a longitudinal axis 21 in order to produce the corresponding spiral shape. For example, such a blade can consist of a foam, be cut correspondingly out of a flat foam material, thereafter be brought into the spiral shape and subsequently heated in order to stabilise the spiral shape after cooling. Thereafter, the body is stable enough to maintain the desired shape during the pump operation but can nevertheless be compressed radially when applying a corresponding compression force.

Figures 5, 6:
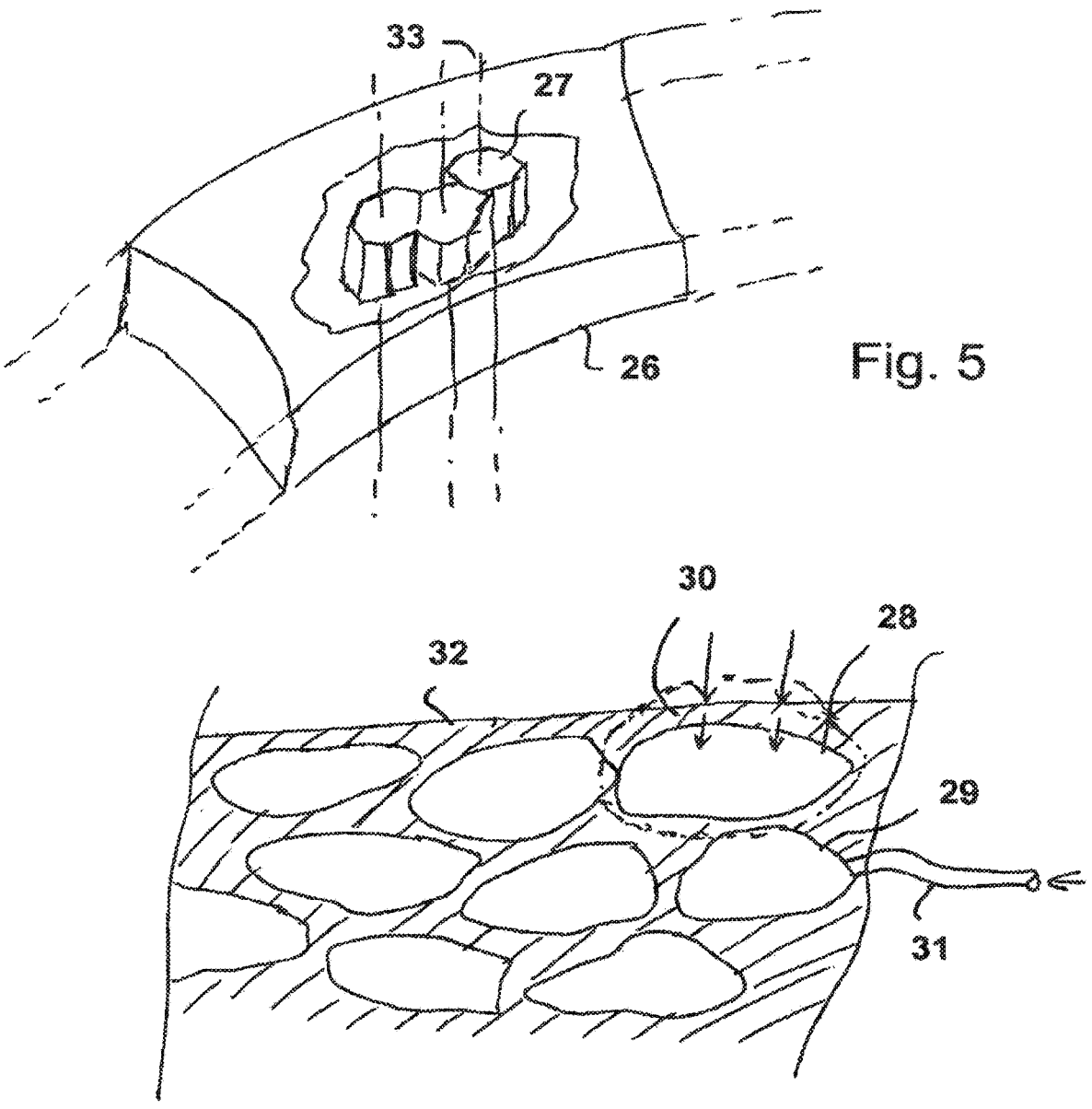

In FIG. 5, a section from a blade 26 is shown schematically, it being illustrated that honeycomb-shaped cavities 27 which have a hexagonal configuration in cross-section are perpendicular to the blade surface by their longitudinal axes 33. In this way, a strongly anisotropic stability can be produced, which leads to the fact that the blade can exert great forces on a fluid in the direction perpendicular to its conveying surface and in the circumferential direction without deforming significantly, that the blade however is more easily compressible by the effect of radial forces with respect to its axis of rotation.

Figure 7:
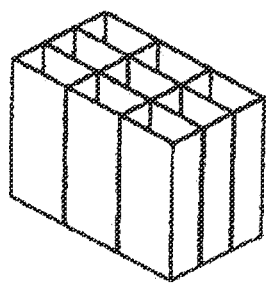
Figure 8:
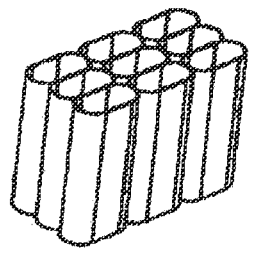
Figure 9:
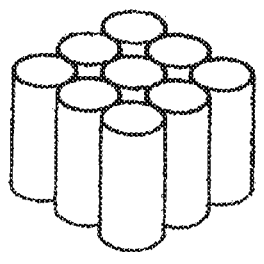
Figure 10:
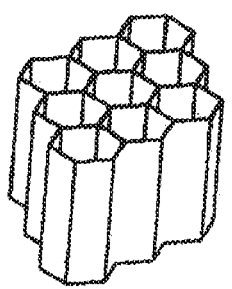
Figure 11:
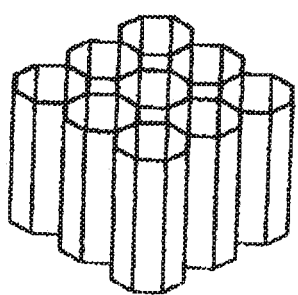

Instead of the honeycomb-shaped cavities 27, also cavities shaped differently in cross-section are conceivable, as are represented in FIGS. 7-11. FIG. 7 thereby shows cuboid cavities, FIG. 8 cavities in strand shape with a rounded cuboid shape, FIG. 9 circular cylinders, FIG. 10 hexagonal honeycomb shapes in the densest packing and FIG. 11 octagonal honeycomb shapes in a dispersed arrangement with square intermediate spaces in cross-section.

Within a hub body which is for instance present, such cavities can for example be aligned in the circumferential direction relative to the axis of rotation 21 of the hub by their longitudinal axes.

FIG. 6 shows, in greatly enlarged, microscopic representation, a foam 32 having closed pores 28, 29, the material of the walls between the pores being configured, in a variant (cavity 28), as semipermeable membrane. Such a membrane allows the diffusion of specific liquids, which can be used for example for an osmotic effect. If the cavities/pores 28 are filled for example with a liquid in which a salt in highly concentrated form is dissolved and if the foam is brought into a liquid which has a lower solution concentration, then the combination tends to bring the concentrations of both liquids to approximate to each other such that the solvent diffuses from outside into the interior of the cavity 28 through the membrane 30. As a result, an increased osmotic pressure is produced and can be used to pump up the cavity 28 into the shape illustrated in broken lines. As a result, an expansion and stiffening of the foam can be achieved.

This effect can be used specifically also for larger cavities in the rotor body. Alternatively, also swelling processes can be used to expand the rotor.

In connection with the cavity 29, a hose 31 is represented and symbolises that corresponding cavities can also be filled with a fluid via individual or collective supply lines or that such a fluid can be suctioned out of them in order to control corresponding decompression/compression processes.

The invention hence produces a rotor which is compressible to a large degree, materials which are already extensively common elsewhere being able to be used for production thereof, which materials have already been tested for the most part also in the medical field. Despite a high possible degree of compression, reliable functioning of a corresponding fluid pump is hence ensured.

The present subject-matter relates, inter alia, to the following aspects:

1. Compressible rotor for a fluid pump having at least one blade and having at least one deformable cavity which is filled or can be filled with a fluid, characterised in that the cavity/cavities is/are delimited at least partially by a partially permeable membrane.
2. Rotor according to aspect 1, characterised in that the cavity/cavities is/are closed.
3. Rotor according to aspect 1 or 2, characterised in that the at least one cavity is filled with a liquid which, in cooperation with the membrane and a liquid in which the pump can be inserted, in particular blood, effects an osmotic diffusion into the cavity with a corresponding increase in pressure.
4. Rotor according to aspect 1 or one of the following, characterised in that a part of the cavities is surrounded by a solid material of the rotor and connected via openings to the exterior and/or to each other.
5. Rotor according to aspect 1 or one of the following, characterised in that the rotor consists at least partially of a porous material, in particular foam.
6. Rotor according to aspect 1 or one of the following, characterised by at least one cavity which has a greater extension in a first direction than in the directions essentially perpendicular thereto.
7. Rotor according to aspect 6, characterised in that the cavity/cavities is/are configured, in cross-section, to be round or polygonal, in particular octagonal, hexagonal, triangular or square.
8. Rotor according to aspect 6 or 7, characterised in that the cavity/cavities have a strand shape.
9. Rotor according to aspect 7 or 8, characterised in that the cavities are orientated with the direction of their greatest stability, in particular their longitudinal axis, in the direction of the pressure forces which arise within the rotor during operation.
10. Rotor according to aspect 1 or one of the following, characterised in that the cavity/cavities is/are provided in at least one blade.
11. Rotor according to aspect 1 or one of the following, characterised in that the blade is configured to be self-supporting and hub-free.
12. Rotor according to one of the aspects 1 to 11, characterised in that the cavity/cavities are provided in a hub body.
13. Fluid pump having a rotor according to one of the aspects 1 to 12, characterised in that a compressible housing surrounding the rotor is provided.
14. Fluid pump according to aspect 13, characterised in that the housing consists at least partially of a material comprising cavities, in particular a foam.
15. Compressible rotor for a fluid pump having at least one blade, the rotor being constructed such that it can adopt a compressed and a decompressed state and the average change in density of the rotor material between compressed and decompressed state is at least 10%.

The invention claimed is:
1. A fluid pump comprising:
a compressible rotor comprising:
   at least one blade; and
   a plurality of anisotropic cavities formed within the at least one blade, each anisotropic cavity having a greater extension in a first direction than in directions perpendicular to the first direction, wherein each of the plurality of anisotropic cavities abuts at least three other anisotropic cavities of the plurality of anisotropic cavities.

2. The fluid pump of claim 1, wherein the plurality of anisotropic cavities is honeycomb-shaped.

3. The fluid pump of claim 1, wherein the plurality of anisotropic cavities is cuboid-shaped, rounded cuboid shaped, circular cylinder-shaped, hexagonal honeycomb-shaped, or octagonal honeycomb-shaped.

4. The fluid pump of claim 1, wherein the plurality of anisotropic cavities includes a first anisotropic cavity, a second anisotropic cavity, a third anisotropic cavity, and a fourth anisotropic cavity, and wherein the first anisotropic cavity abuts the second anisotropic cavity, the third anisotropic cavity, and the fourth anisotropic cavity.

5. The fluid pump of claim 1, wherein the at least one blade is configured to be self-supporting and hub-free.

6. The fluid pump of claim 1, wherein the compressible rotor further includes a hub to which the at least one blade connects.

7. The fluid pump of claim 6, wherein the hub includes at least one deformable cavity formed therein.

8. The fluid pump of claim 1, further comprising a compressible housing surrounding the compressible rotor.

9. The fluid pump of claim 8, wherein the compressible housing includes at least one deformable cavity formed therein.

10. The fluid pump of claim 1, wherein each of the plurality of anisotropic cavities has a longitudinal axis oriented perpendicular to a conveying surface of the at least one blade.

11. The fluid pump of claim 1, wherein the at least one blade includes a porous material.

12. The fluid pump of claim 11, wherein the porous material is foam.

13. The fluid pump of claim 1, wherein the fluid pump is a blood pump.

14. The fluid pump of claim 1, wherein the plurality of anisotropic cavities allows the at least one blade to exert force on a conveyed fluid without significant deformation of the at least one blade.

* * * * *